(12) United States Patent
Baid

(10) Patent No.: US 10,813,579 B2
(45) Date of Patent: *Oct. 27, 2020

(54) BLOOD COLLECTION DEVICE

(71) Applicant: Poly Medicure Limited, Faridabad (IN)

(72) Inventor: Rishi Baid, New Delhi (IN)

(73) Assignee: Poly Medicure Limited, Faridabad (IN)

( * ) Notice: Subject to any disclaimer, the term of this patent is extended or adjusted under 35 U.S.C. 154(b) by 397 days.

This patent is subject to a terminal disclaimer.

(21) Appl. No.: 15/849,516

(22) Filed: Dec. 20, 2017

(65) Prior Publication Data

US 2018/0160958 A1  Jun. 14, 2018

Related U.S. Application Data

(63) Continuation-in-part of application No. 13/394,638, filed on Mar. 7, 2012, now Pat. No. 9,877,675.

(51) Int. Cl.
*A61B 5/15* (2006.01)
*A61B 5/153* (2006.01)

(52) U.S. Cl.
CPC .... *A61B 5/150213* (2013.01); *A61B 5/15003* (2013.01); *A61B 5/1535* (2013.01); *A61B 5/150496* (2013.01); *A61B 5/150259* (2013.01); *A61B 5/150389* (2013.01); *A61B 5/150572* (2013.01)

(58) Field of Classification Search
USPC ......................................................... 600/579
See application file for complete search history.

(56) References Cited

U.S. PATENT DOCUMENTS

| 5,520,193 | A  | * | 5/1996  | Suzuki  | A61B 5/150396 600/577 |
| 6,355,023 | B1 | * | 3/2002  | Roth    | A61M 5/1409 604/411 |
| 2004/0210247 | A1 | * | 10/2004 | Sonoda  | A61B 5/14532 606/181 |
| 2005/0004524 | A1 | * | 1/2005  | Newby   | A61M 5/3243 604/164.08 |

* cited by examiner

*Primary Examiner* — Daniel L Cerioni
(74) *Attorney, Agent, or Firm* — IP Attorneys Group, LLC

(57) ABSTRACT

The application relates to a blood collection device comprising: a cannula hub defining a chamber; an in-let cannula defining an axis and having a distal end and a lumen extending therethrough, the inlet cannula being mounted to the cannula hub such that the distal end of the inlet cannula is external of the cannula hub and such that the lumen through the inlet cannula communicates with the chamber; an outlet cannula having a proximal end and a lumen extending therethrough, the outlet cannula being mounted to the cannula hub such that the proximal end of the outlet cannula is external of the cannula hub and such that the lumen of the outlet cannula communicates with the chamber; a closed sleeve mounted over a portion of the outlet cannula disposed externally of the cannula hub; and a venting mechanism providing communication between the chamber and ambient surroundings.

5 Claims, 2 Drawing Sheets

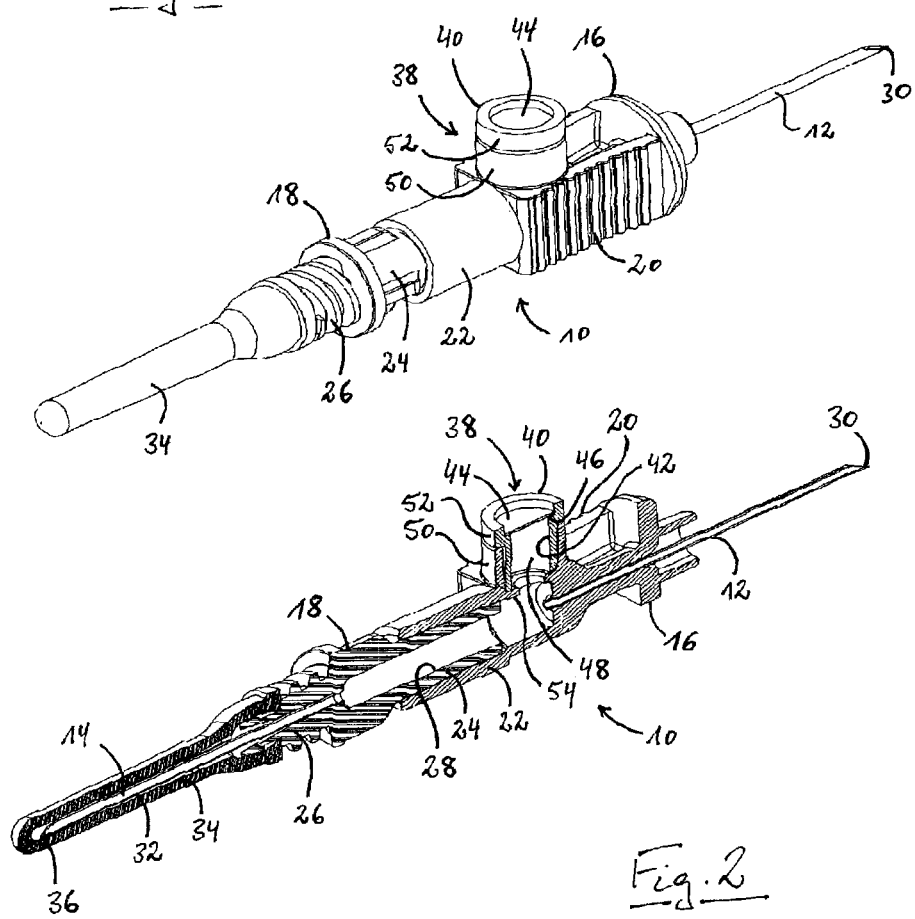

BLOOD COLLECTION DEVICE

CROSS REFERENCE TO RELATED APPLICATIONS

This application is a continuation in part of U.S. application Ser. No. 13/394,638, filed Mar. 7, 2012.

INCORPORATION BY REFERENCE

The above referenced application, U.S. application Ser. No. 13/394,638, filed Mar. 7, 2012, published as US 2012/0172754 A1, is incorporated herein by reference in its entirety, including drawings and appendices, and hereby made a part of this application.

BACKGROUND OF THE INVENTION

The invention relates to a blood collection device comprising a cannula hub defining a chamber, an inlet cannula and an outlet cannula both being mounted to the cannula hub and communicating with the chamber, a closed sleeve mounted over a portion of the outlet cannula disposed externally of the cannula hub, and a venting mechanism providing communication between the chamber and ambient surroundings.

Blood collection devices of the above kind have long been used to collect blood from patients, wherein the patients' vessels from which blood is to be drawn are often rather small and/or not visible. If the tip of the inlet cannula is not in communication with the interior of the blood vessel, the procedure of collecting blood is likely to be unsuccessful and the patient may be harmed additionally by the penetration of delicate underlying structures. Accordingly, conformation of accurate placement of the cannula tip into a blood vessel is desirable for blood drawing procedures.

Known intravenous blood collection devices therefore include mechanisms for indicating when the inlet cannula tip is in communication with the interior of a blood vessel, for example, a transparent portion of the cannula hub from which the presence of blood can be observed. The observation of blood in the cannula hub is known as "flashback". However, flashback detection has been less than satisfactory for many such blood collection devices, since the flow of blood into the transparent portion of the cannula hub is impeded by air backpressure in the cannula hub and, thus, flashback confirmation is not visible or delayed. This delay can impede the determination of the precise moment at which the cannula tip enters the blood vessel, which may cause the healthcare worker inserting the needle to miss or perforate the vessel and penetrate into delicate surrounding structures. Accordingly, intravenous blood collection devices have been provided with a venting mechanism providing communication between a flashback chamber of the cannula hub and ambient surroundings.

SUMMARY OF THE INVENTION

It is an object of the present invention to provide a blood collection device which allows for an easy handling and which is inexpensive to manufacture.

This object is satisfied by a blood collection device in accordance with claim 1.

The blood collection device of the invention comprises a cannula hub defining a chamber, a cannula defining an axis and having a distal end, a proximal end and a lumen extending therethrough. The cannula is mounted to the cannula hub such that the distal end and the proximal end of the cannula are external of the cannula hub and such that the lumen through the cannula communicates with the chamber by means of an opening. The blood collection device further comprises a closed sleeve mounted over a portion of the cannula disposed externally of the cannula hub and a venting mechanism providing communication between the chamber and ambient surroundings, the venting mechanism comprising a tubular insert defining a fluid passage therethrough and a membrane extending across the fluid passage, wherein the membrane is made from a material permeable for air and substantially impermeable for blood. The blood collection device is characterized in that the tubular insert is received in a tubular projection extending from the cannula hub such that the end of the tubular insert facing towards the flashback chamber abuts on the inner collar when the tubular insert is fully inserted into the tubular projection, whereby the inner collar is provided in the transition region from the tubular projection to the flashback chamber. The blood collection device is further characterized in that the cannula hub is formed from first and second parts. The first part comprises a grip portion and a tubular portion extending proximal therefrom in the direction of the cannula axis and the second part is of generally tubular shape and partly received in the tubular portion of the first part by means of a press fit.

Due to the press fit, the second part needs only to be pushed into the first part for assembly of the device, which adds to the simple and cost effective manufacturing of the device.

The blood collection device of the invention and, in particular, the specific design of its venting mechanism allows blood flashback to occur particularly rapidly upon entry of the inlet cannula into the blood vessel. This makes particularly quick and reliable venipuncture detection possible and, thus, helps to ensure that the inlet cannula is correctly placed in the patient on the first try. In the end, blood can be collected with the device of the invention in a manner that is particularly gentle on the patient.

According to the invention, the inlet cannula and the outlet cannula can either be two separate parts or they can be integrally formed from a single cannula that is provided with an opening in the region of the flashback chamber which allows for communication between both the lumen of the inlet cannula and the lumen of the outlet cannula with the flashback chamber.

Furthermore, the membrane can be configured such that upon contact with blood the membrane either remains permeable for air or becomes impermeable not only for blood but also for air. In the latter case the membrane could be referred to as self-sealing.

Preferably, the tubular projection extends in a direction transverse, in particular perpendicular, to the axis of the inlet cannula.

The manufacturing of the device is particularly simple and inexpensive, if the tubular projection is integral with the cannula hub, in particular with a first part of the cannula hub carrying the inlet cannula.

According to an embodiment, the tubular insert of the venting mechanism is fixed in the tubular projection by means of a press fit. This makes the assembly of the device particularly simple and cost effective, since the venting mechanism can be prepared separately from the cannula hub, whereupon the tubular insert has merely to be pushed into the tubular projection.

In order to prevent the tubular insert from being pushed too far into the tubular projection, the tubular insert of the venting mechanism may have a collar formed on its outer surface adjacent an end facing away from the cannula hub. In addition, the collar fulfils a sealing function as it helps to prevent blood from exiting the flashback chamber.

Preferably, an outer diameter of the collar is substantially equal to an outer diameter of the tubular projection, since this leads to a smooth transition from collar to tubular projection in the assembled state.

According to a further embodiment, the fluid passage is diminished by an inner collar in the region of the tubular projection adjacent the chamber of the cannula hub. This inner collar adds to the sealing function in that it also helps to prevent blood from exiting the flashback chamber.

The grip portion makes the handling of the device easier, while the tubular portion extending therefrom may be designed to give a clear view on blood entering the flashback chamber.

Preferably, the second part and at least the tubular portion of the first part are made from a transparent plastic material. This simplifies flashback detection and makes the manufacturing of the device even more cost effective, since the first and second parts can be made by injection molding and no additional windows for flash back detection have to be implemented.

BRIEF DESCRIPTION OF THE DRAWINGS

FIG. 1 is a perspective view of a blood collection device in accordance with the invention;

FIG. 2 is a cross sectional view of the blood collection device of FIG. 1; and

DETAILED DESCRIPTION OF THE INVENTION

Figure 3:
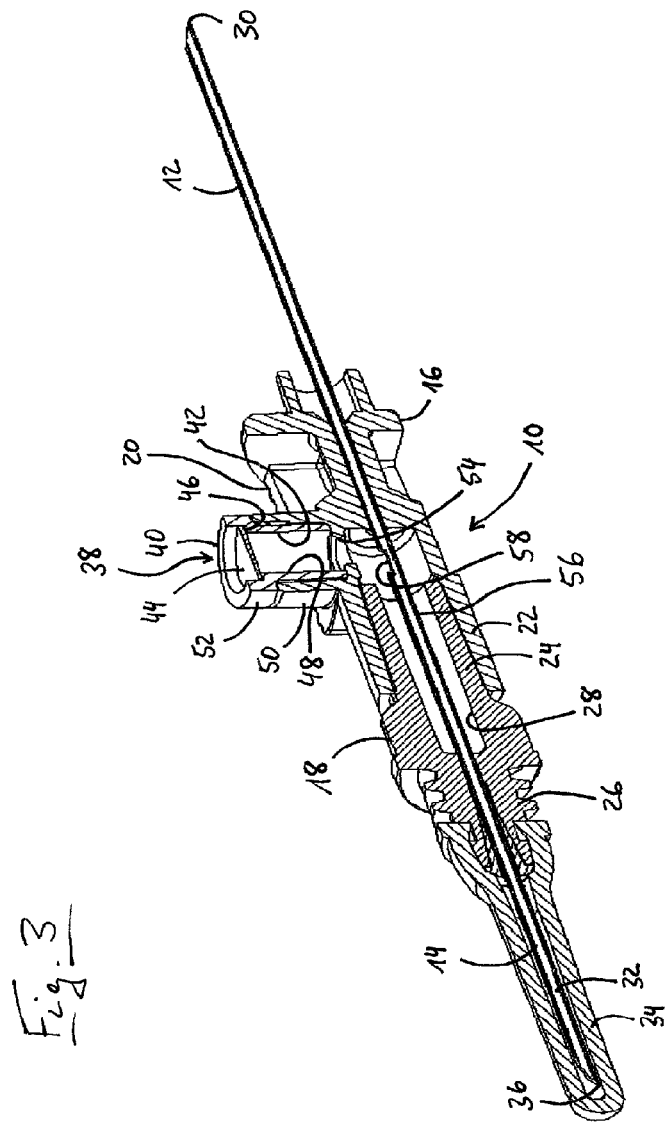
FIG. 3 is a cross sectional view of a blood collection device according to a further embodiment of the invention.

The blood collection device shown in FIGS. 1 and 2 comprises a cannula hub 10 which carries an inlet cannula 12 and an outlet cannula 14. Inlet and outlet cannulas 12, 14 are aligned and define a needle axis. According to this embodiment, the inlet cannula 12 and the outlet cannula 14 form separate parts.

The cannula hub 10 is formed from a first part 16 and a second part 18. Both the first and second parts 16, 18 are made from a transparent plastic material, e.g. by injection molding.

The first part 16 includes a distal grip portion 20 for easy handling of the blood collection device, and a tubular portion 22 extending proximal therefrom.

The second part 18 includes a tubular portion 24 and a threaded portion 26 extending proximal therefrom. The tubular portion 24 of the second part 18 has a slightly tapered outer surface and is received in the tubular portion 22 of the first part 16 by means of a press fit. The threaded portion 26 makes it possible to attach a blood collection tube, bag, container or the like (not shown) to the device.

The tubular portions 22, 24 of the first and second parts 16, 18 together define a flashback chamber 28 of the cannula hub 10.

The inlet cannula 12 has a tip 30 at its distal end which is adapted to be inserted into a patient's blood vessel for drawing blood. The inlet cannula 12 is mounted to the first part 16 of the cannula hub 10 such that its lumen communicates with the flashback chamber 28.

The outlet cannula 14 is mounted to the second part 18 of the cannula hub 10 such that a lumen of the outlet cannula 14 communicates with the flashback chamber 28. The outlet cannula 14 has a proximal portion 32 extending from the second part 18 of the cannula hub 10 which is adapted to be inserted into an blood collection tube, bag, container or the like (not shown) for collecting blood from the flashback chamber. The proximal portion 32 of the outlet cannula 14 is covered by a rubber sleeve 34. The outlet cannula 14 has a tip 36 at its proximal end for puncturing the rubber sleeve 34 when the blood collection tube, bag, container or the like is to be connected to the device.

The blood collection device further comprises a venting mechanism 38 providing communication between the flashback chamber 28 and ambient surroundings.

The venting mechanism 38 comprises a tubular insert 40 defining a fluid passage 42 therethrough, and a membrane 44 extending across the fluid passage 42. The membrane 44 sits on a shoulder 46 extending along the inner surface 48 of the tubular insert 40 and may be attached to the tubular insert 40, for example, by gluing, welding, etc.

The membrane 44 is made from a material permeable for air and substantially impermeable for blood. The membrane 44 can be configured such that upon contact with blood the membrane 44 either remains permeable for air or becomes impermeable not only for blood but also for air. Examples for suitable materials include but are not limited to plastic, thermoplastic and polyethylene.

The tubular insert 40 of the venting mechanism 38 is received in a tubular projection 50 which is formed integral with the first part 16 of the cannula hub 10. The tubular projection 50 extends perpendicularly to the needle axis from the first part 16 of the cannula hub 10, more specifically in the proximal region of the grip portion 20 thereof.

The tubular insert 40 of the venting mechanism 38 is fixed in the tubular projection 50 by means of a press fit. An outer collar 52 is formed at an outer surface of the tubular insert 40 adjacent an end of the tubular insert 40 facing away from the cannula hub 10. The outer diameter of the collar 52 is substantially equal to an outer diameter of the tubular projection 50.

In the transition region from the tubular projection 50 to the flashback chamber 28, an inner collar 54 is provided. The length of the tubular insert 40 is selected such that the outer collar 52 abuts on the end of the tubular projection 50 facing away from the flashback chamber 28, while the end of the tubular insert 40 facing towards the flashback chamber 28 abuts on the inner collar 54, when the tubular insert 40 is fully inserted into the tubular projection 50.

In use, when the inlet cannula 12 is inserted into the blood vessel of a patient blood enters the inlet cannula 12 due to the blood pressure, thereby displacing air from the lumen of the inlet cannula 12 into the flashback chamber 28. Instead of being compressed in the flashback chamber 28 and thereby building up backpressure, the displaced air can escape from the flashback chamber 28 via the membrane 44 of the venting mechanism 38, such that the blood in the inlet cannula 12 is free to flow into the flashback chamber thereby indicating successful venipuncture. At the same time, membrane 44 as well as the press fit of the tubular insert 40 in the tubular projection 50 together with the outer and inner collars 52, 54 prevent blood from escaping the flashback chamber 28 via the venting mechanism 38.

FIG. 3 illustrates another embodiment of a blood collection device in accordance with the invention, which is essentially identical to the blood collection device shown in FIGS. 1 and 2 except for the fact that the inlet cannula 12 and the outlet cannula 14 do not form separate parts. Instead, in the blood collection device of FIG. 3 the inlet cannula 12 and the outlet cannula 14 are integrally formed from a single cannula 56 provided with an opening 58 that not only distinguishes the inlet cannula 12 from the outlet cannula 14 but also allows for communication between both the lumen of the inlet cannula 12 and the lumen of the outlet cannula 14 with the flashback chamber 28. The opening 58, e.g. a slot or a puncture, can be positioned anywhere in the region of the flashback chamber 28.

LIST OF REFERENCE NUMERALS 10 cannula hub
12 inlet cannula
14 outlet cannula
16 first part
18 second part
20 grip portion
22 tubular portion
24 tubular portion
26 threaded portion
28 flashback chamber
30 tip
32 proximal portion
34 rubber sleeve
36 tip
38 venting mechanism
40 tubular insert
42 fluid passage
44 membrane
46 shoulder
48 inner surface
50 tubular projection
52 outer collar
54 inner collar
56 single cannula
58 opening

What is claimed is:

1. A blood collection device comprising:
a cannula hub (10) defining a chamber (28);
a cannula (56) defining an axis and having a distal end, a proximal end and a lumen extending therethrough, the cannula (56) being mounted to the cannula hub (10) such that the distal end and the proximal end of the cannula (56) are external of the cannula hub (10) and such that the lumen through the cannula (56) communicates with the chamber (28) by means of an opening (58);
a closed sleeve (34) mounted over a portion (32) of the cannula (56) disposed externally of the cannula hub (10); and
a venting mechanism (38) providing communication between the chamber (28) and ambient surroundings, the venting mechanism (38) comprising a tubular insert (40) defining a fluid passage (42) therethrough and a membrane (44) extending across the fluid passage (42), wherein the membrane (44) is made from a material permeable for air and substantially impermeable for blood;
wherein the tubular insert (40) is received in a tubular projection (50) extending from the cannula hub (10) such that a end of the tubular insert (40) facing towards the flashback chamber (28) abuts on an inner collar (54) when the tubular insert (40) is fully inserted into the tubular projection (50), whereby the inner collar (54) is provided in a transition region from the tubular projection (50) to the flashback chamber (28),
the cannula hub (10) is formed from first and second parts (16, 18),
the first part (16) comprises a grip portion (20) and a tubular portion (22) extending proximal therefrom in a direction of the cannula axis, and
the second part (18) is of tubular shape and partly received in the tubular portion (22) of the first part by means of a press fit.

2. The blood collection device in accordance with claim 1, wherein the tubular insert (40) of the venting mechanism (38) is fixed in the tubular projection (50) by means of a press fit.

3. The blood collection device in accordance with claim 1, wherein the second part (18) and at least the tubular portion (22) of the first part (16) are made from a transparent plastic material.

4. The blood collection device according to claim 1, wherein the cannula (56) defining an axis is formed from a single cannula (56) having a distal end, a proximal end and a lumen extending therethrough.

5. The blood collection device according to claim 4, wherein the cannula (56) is provided with an opening (58), in particular wherein the lumen through the cannula (56) communicates with the chamber (28) by means of the opening (58).

* * * * *